(12) United States Patent
Das et al.

(10) Patent No.: US 6,227,261 B1
(45) Date of Patent: May 8, 2001

(54) METHOD AND APPARATUS FOR THE ADDITION OF STERILE LIQUID TO AN ASEPTIC SYSTEM

(75) Inventors: Wilfred Das, Gurnee; John McDonald, Libertyville, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/220,782

(22) Filed: Dec. 24, 1998

(51) Int. Cl.$^7$ ........................................................ B65B 1/04
(52) U.S. Cl. .................................. 141/1; 141/94; 141/83; 141/284
(58) Field of Search .............................. 141/1, 2, 18, 94, 141/83, 99–104, 285

(56) References Cited

U.S. PATENT DOCUMENTS 4,563,170   1/1986   Aigner et al. .

FOREIGN PATENT DOCUMENTS

| 4203905 | 8/1993 | (DE) . |
| 0722744 | 7/1996 | (EP) . |
| 9636370 | 11/1996 | (WO) . |

OTHER PUBLICATIONS

Database WPI Section Ch, Week 199533—Derwent Publications Ltd., London, GB; Class B04, AN 1995–253233, XP002137116 & RU 2 026 723 C (Appl Microbiology Res Inst), Jan. 20, 1995 abstract.
Patent Abstracts of Japan vol. 1998, No. 14, Dec. 31, 1998 & JP 10 230260 A Sep. 2, 1998 abstract—Patent Abstracts of Japan JP 10 230260 A Sep. 22, 1998, figure 1.
Patent Abstracts of Japan vol. 1995, No. 01 Feb. 28, 1995 & JP 06 292546 A, Oct. 21, 1994, abstract.

*Primary Examiner*—Steven O. Douglas
(74) *Attorney, Agent, or Firm*—Brian R. Woodworth

(57) ABSTRACT

An apparatus for adding a quantity of a sterile liquid to a processing system. The apparatus includes an additive reservoir constructed to retain a liquid therein and a first flow channel having a first end portion fluidly connected to the additive reservoir and having a second end portion constructed for fluid connection to a processing system. The apparatus further includes a container constructed to retain a liquid therein and a second flow channel having a first end portion fluidly connected to the container and having a second end portion in fluid communication with the additive reservoir. A filter constructed to sterilize a liquid flowing through the second flow channel is provided. A first valve constructed to control flow through said second flow channel also is included in the apparatus.

8 Claims, 2 Drawing Sheets

METHOD AND APPARATUS FOR THE ADDITION OF STERILE LIQUID TO AN ASEPTIC SYSTEM

TECHNICAL FIELD

The present invention relates generally to the preparation of emulsions, solutions, and other liquid compounds, and more particularly to a method and an apparatus for the addition of a sterile liquid to an aseptic processing system.

BACKGROUND OF THE INVENTION AND TECHNICAL PROBLEMS POSED BY THE PRIOR ART

The preparation of sterile liquid compounds, including emulsions and solutions, is well known. In certain cases it is necessary to sterilize the resulting liquid compound prior to using it for its intended purpose. Sterile filtration and heat-processing are well-known techniques for the terminal sterilization of such liquid compounds.

In certain situations it is preferable to provide a system that aseptically produces the liquid compound, thereby obviating the need for terminal sterilization of the compound. For example, it is possible that terminal sterilization will damage certain characteristics of the liquid compound. In the course of aseptic processing of a liquid compound it is usually necessary to add components of the compound into the aseptic processing system, thus requiring that each added component be sterile when it is introduced into the system. However, in many cases one or more of these components is provided in a non-sterile form. In order to ensure that each component is sterile when it enters the processing system, a sterilizing-grade filter or other known sterilization process can be used to sterilize the ingredient immediately prior to its introduction into the system.

It is difficult to ensure the accurate delivery of a pre-measured amount of a component when a sterilizing-grade filter is used due to the fact that the filter tends to retain a quantity of the component during filtration. In order to overcome this shortcoming of sterile filtration techniques, some prior art systems have employed a pre-sterilized hypodermic syringe to introduce sterile ingredients into a septum or injection site associated with the processing system. However, this technique can be cumbersome and is prone to failure due to the need to maintain the sterility of both the syringe and the septum or injection site, as well as the need to sterilize the component prior to its introduction into the hypodermic syringe.

The present invention contemplates an arrangement whereby a sterile ingredient that has been sterilized through the use of a sterile-grade filter can be efficiently and accurately added to a processing system, such as that used in the production of a sterile emulsion.

SUMMARY OF THE INVENTION

The present invention is directed to an apparatus, and a method, for adding a selected quantity of a sterilized liquid to an aseptic processing system. The apparatus of the present invention employs an additive reservoir which is fluidly connected to a liquid container. The additive reservoir is constructed to retain a sterile liquid therein prior to addition of the sterile liquid into a processing system. A filter is provided to sterilize liquid as it flows from the liquid container into the additive reservoir. A fill valve is provided between the liquid container and the additive reservoir in order to control flow therebetween. The additive reservoir is constructed to be fluidly connected to an aseptic processing system.

In one embodiment of the present invention, an addition valve is interposed between the additive reservoir and the processing system to which a measured quantity of sterile liquid is to be added, the addition valve being constructed to control flow between the additive reservoir and the system.

In another embodiment of the apparatus of the present invention, the additive reservoir includes a vent for venting the additive reservoir when liquid flows to or from the reservoir. In this embodiment, a sterile gas filter preferably is provided in order to filter the gas before it enters the additive reservoir, thereby maintaining sterility within the reservoir.

Other features and advantages of the present invention will become readily apparent from the following detailed description, the accompanying drawings, and the appended claims.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

Figure 1:
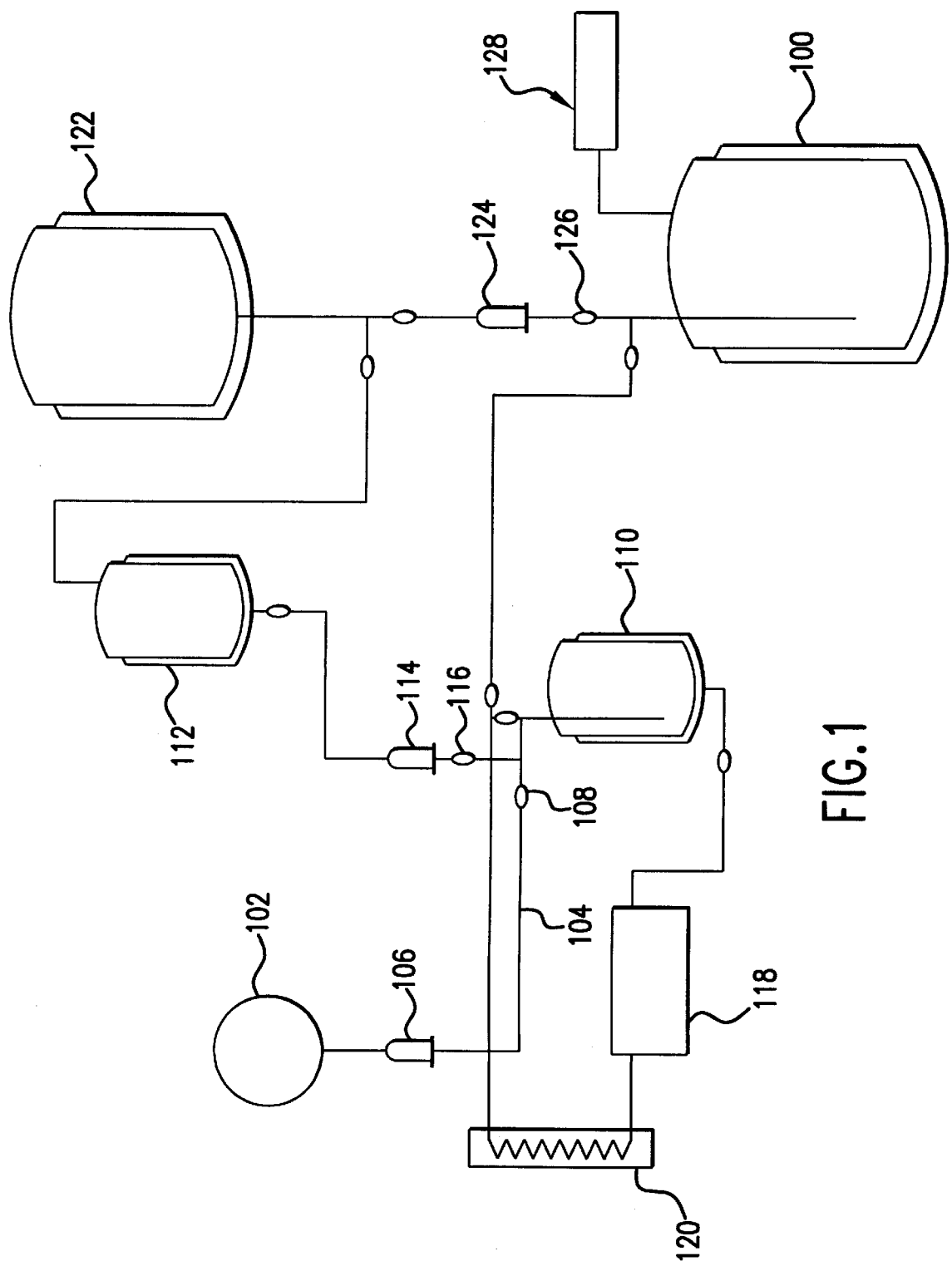
FIG. 1 is a diagrammatic view of a system for processing a sterile liquid, wherein the system includes an arrangement for adding a sterile liquid component to the system.

While the present invention is susceptible of embodiment in various forms, there is shown in the drawings, and will hereinafter be described, a presently preferred embodiment, with the understanding that the present disclosure is to be considered as an exemplification of the invention and is not intended to limit the invention to the specific embodiment illustrated. The scope of the present invention is defined by the appended claims.

With reference first to FIG. 1, therein is illustrated an exemplary system for the production of a sterile liquid compound, in this case, the production of a sterile emulsion. The system illustrated in FIG. 1 has been particularly configured for the production of a sterile, heat-labile liquid composition that does not lend itself to terminal sterilization for achieving the desired degree of sterility of the final product. As such, the system has been configured to process aseptically the various components of the liquid composition, including an aseptic homogenizer that has been particularly configured to maintain the sterility of the liquid being formulated. Co-pending U.S. patent application Ser. No. 09/220,426, filed Dec. 24, 1998 more particularly discloses the system illustrated in FIG. 1, which patent application is hereby incorporated by reference.

As shown in FIG. 1, the system includes a container 100 into which the components of the liquid composition being formed are directed. It will be appreciated that the liquid composition can contain any number of components. In the embodiment of the present invention depicted in FIG. 1, a first component of the liquid composition is provided in first component container 102 which is fluidly connected to flow channel 104. In the depicted embodiment, a sterile filter 106 is provided between container 102 and flow channel 104 in order to sterile filter the first component as it flows from container 102 into flow channel 104. Sterile-grade filters of the type employed in the present invention are well known in the art, as is the technique for selecting a sterile-grade filter for use in sterilizing liquids having different characteristics. Valve 108 is provided in flow channel 104 in order to control the flow of the first component therethrough. Flow channel 104 is fluidly connected to a first processing container 110.

A second component of the liquid composition is provided in second component container 112. Second component container 112 also is fluidly connected to first processing container 110. In the embodiment of the present invention depicted in FIG. 1, second component container 112 is fluidly connected to flow channel 104 at a position downstream of valve 108. However, it will be appreciated that second component container 112 can be fluidly connected directly to first processing container 110. In the depicted embodiment, sterile filter 114 is provided between container 112 and flow channel 104 in order to sterile filter the second component as it flows from container 112 into first processing container 110. Valve 116 is included in the flow path of the second component from container 112 and first processing container 110 in order to control flow of the second component into first processing container 110.

In the embodiment of the present invention depicted in FIG. 1, the first and second components are received in first processing container 110. Thereafter, a variety of known processes can be performed on the first and second components, such processes being performed in first processing container 110 and/or downstream thereof. For example, an aseptic homogenizer 118 can be provided in order to homogenize the first and second components. Further, a heat exchanger 120 can be provided in order to facilitate further processing, e.g., temperature control, of the homogenized first and second components. Following the selective processing of the first and second components, they are introduced into container 100 for further processing or withdrawal from the system.

In the embodiment of the invention depicted in FIG. 1, a third component of the liquid composition is provided in third component container 122. Third component container 122 is fluidly connected to container 100. Sterile filter 124 is provided between container 122 and container 100 in order to sterile filter the third component as it flows from container 122 into container 100. Valve 126 is included in the flow path of the third component between container 122 and container 100 in order to control flow of the third component.

The embodiment depicted in FIG. 1 further includes a pH adjustment system 128. The pH adjustment system will be described in detail herein in connection with FIG. 2. However, it is to be appreciated that an apparatus such as system 128 can be employed for the introduction of any or all of the components of the liquid composition produced by the system of the present invention. That is, system 128, as described herein, can be used in connection with the addition of any one or more of the first, second, and third components of the liquid composition produced using the system depicted in FIG. 1. Utilization of system 128 in connection with the sterile addition of one or more components will be apparent from the following, detailed description of system 128.

Figure 2:
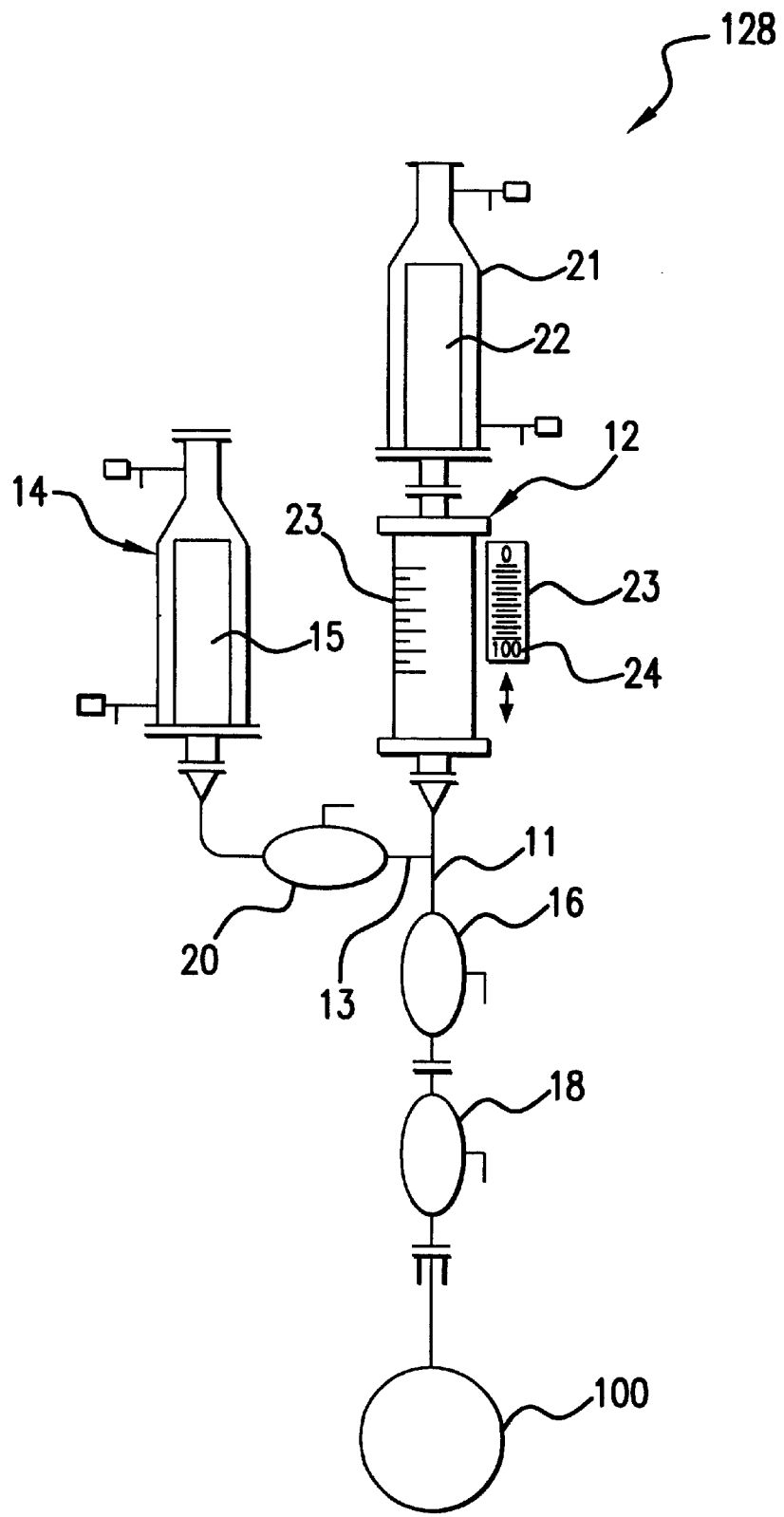
FIG. 2 is a more detailed, diagrammatic view illustrating the system of the present invention.

As shown in FIG. 2, system 128 includes an additive reservoir 12 in which a sterile liquid (in this case, an acidic or basic liquid employed for the purpose of adjusting the pH of the liquid in the system) is temporarily held prior to introduction into the system through first fluid conduit 11. Additive reservoir 12 is fluidly connected to a source container 14 through a second fluid conduit 13. As above-discussed, source container 14 can hold any component of a sterile liquid composition processed by the system of the present invention.

Filter 15 is provided in order to sterile filter the pH adjustor prior to its introduction into additive reservoir 12. In the depicted embodiment, filter 15 is positioned within source container 14 such that liquid in source container 14 flows through filter 15 prior to entering second fluid conduit 13. However, it will be appreciated that filter 15 can be positioned at any position along the length of second fluid conduit 13. It also will be appreciated that the structure and performance characteristics of filter 15, as well as the structure and performance characteristics of filters 106, 114, and 124, as discussed in detail herein, will be dependent upon the characteristics of the liquid that is passed therethrough and the particular needs of the system, e.g., molecule size and prevention of microbial ingress/egress. One of ordinary skill in the relevant art will readily understand how to select filters for use in connection with the processing of specific liquids.

In the depicted embodiment, addition valve 16 is provided in first flow channel 11 between reservoir 12 and container 100 in order to control flow therebetween. Fill valve 20 is provided in second flow channel 13 between container 14 and reservoir 12 in order to control flow therebetween. Addition valve 16 and fill valve 20, as well as valves 108, 116, and 124, can be of any known construction. In a preferred embodiment of the present invention, one or more of valves 16, 20, 108, 116, and 124 are two-way in nature and are selectively operable, e.g., manually, hydraulically, or electronically, such that a selected amount of liquid can be controllably moved therethrough and such that flow can be shut off after the selected amount of liquid has passed therethrough. In the embodiment of the present invention depicted in FIG. 2, an isolation valve 18 is provided for facilitating further isolation of reservoir 12 from container 100.

In the depicted embodiment, second flow channel 13 is fluidly connected to first flow channel 11 at a position downstream from reservoir 12. However, it will be appreciated that second flow channel 13 can be fluidly connected directly to reservoir 12 or at a position upstream from reservoir 12 (but downstream from filter 21, as discussed herein) without departing from the intended spirit and scope of the present invention.

With respect to the movement of liquids through the system of the present invention, it will be appreciated that movement can be provided as a result of gravity, pressure differentials, and/or pumps of known construction without departing from the intended spirit and scope of the present invention. In connection with the embodiment of the present invention depicted in the accompanying figures, pressurized gas is used in order to create a pressure differential between reservoir 12 and container 100, thereby facilitating the introduction of sterile liquids from reservoir 12 into container 100.

As sterile liquid flows into and from reservoir 12, it is desirable to maintain the sterility of the reservoir 12, while at the same time venting gas out of or forcing sterile gas into the reservoir to the facilitate the free flow of liquid. To this end, apparatus 10 includes a vent 21 having a gas filter 22. Gas filter 22 is constructed so as to ensure that gases flowing into reservoir 12 are sterile. As above-discussed, the characteristics of gas filter 22 will be dependent upon the characteristics of the gas used, e.g., air or nitrogen. The reservoir 12 is in fluid communication with the vent 21 and the gas filter 22 so that as liquid flows into the reservoir 12 via fill valve 20, gas can be vented out of the reservoir 12 to the atmosphere, and so that as liquid flows out of the reservoir 12 and into container 100, gas can be forced into reservoir 12 in order to provide a pressure differential between reservoir 12 and container 100. A regulated gas supply can be provided in operative connection with the vent 21 for supplying pressurized gas to the reservoir 12.

Efficient operation of the present apparatus is facilitated by the provision of a suitable calibration scale 23 in operative association with the reservoir 12. The calibration scale is selected such that it precisely indicates the quantity of liquid contained in and/or delivered from reservoir 12. If desired, the calibration scale 23 can be provided on the reservoir, thus facilitating monitoring of the quantity of liquid that flows from the reservoir into the associated system. Alternatively, the calibration scale 23 for the reservoir 12 can be provided in the form of movable calibration scale 24. The provision of the movable scale further facilitates efficient operation of the apparatus in that the calibration scale can be zeroed to a level corresponding to the sterile liquid positioned within the additive reservoir 12 prior to the introduction of the sterile liquid from the reservoir 12 into the associated system.

Sterility of the additive reservoir 12, the sterilizing filters 15 and 22, and the associated flow channels, can be achieved during sterilization of the associated system, such as by steam sterilization or the like. When it is desired to effect the addition of a measured quantity of sterile liquid to the system, a quantity of the liquid in container 14 is directed through sterile additive filter 15 by placing fill valve 20 in an open position. Addition valve 16 is closed during this step of the process in order to enable more precise measurement of the quantity of liquid added to the processing system. Filter 15 is constructed such that the liquid is sterilized after it has passed therethrough. Because of the inevitable retention of at least some of the liquid within the sterile filter 15, the initial quantity of the liquid directed from container 14 and through filter 15 is preferably selected to be at least slightly greater than the final, measured quantity of the liquid to be added to container 100 from additive reservoir 12.

After the sterile liquid flows through fill valve 20 into reservoir 12, the fill valve 20 is closed. An operator of the apparatus can either observe the level of the sterile liquid within the reservoir with respect to the calibration scale 23 provided thereon, or can effect movement of movable scale 24 for zeroing the scale with respect to the level of sterile liquid in the reservoir. By observing the initial volume in the reservoir as shown by the calibration 23, and by noting the calibration mark at which the required measured quantity will have been added to the associated system, an operator can easily add an exact, measured quantity of the liquid by opening addition valve 16, as well as isolation valve 18, between the reservoir 12 and container 100. Fill valve 20 preferably is maintained in a closed condition during this step of the process. Liquid in reservoir 12 can be introduced into container 100, or any other portion of a selected system, through the use of gravity, pumps, and/or other pressure differentials. For example, pressurized gas can be introduced into vent 21 such that sterile, pressurized gas is introduced into reservoir 12 in order to force the liquid contained therein into container 100. The pressure generated in reservoir 12 is preferably greater than a fluid pressure within container 100, or the associated system, in order to enable the introduction of liquid from reservoir 12.

Connection of the present apparatus to a system, e.g., container 100, via isolation valve 18 permits the reservoir 12 and associated sterile filters, to be removed from the associated container for use elsewhere or replacement, as may be required from time-to-time.

From the foregoing, it will be observed that numerous modifications and variations can be effected without departing from the true spirit and scope of the novel concept of the present invention. No limitation with respect to the specific embodiments illustrated herein is intended or should be inferred. The disclosure is intended to cover, by the appended claims, all such modifications as fall within the scope of the claims.

What is claimed is:

1. An apparatus for adding a quantity of a sterile liquid to a processing system, said apparatus comprising:
    an additive reservoir constructed to retain a liquid therein;
    a vent having a gas filter constructed to sterilize a gas flowing through said vent, said vent disposed in fluid communication with said additive reservoir;
    a first flow channel having a first end portion fluidly connected to said additive reservoir, said first flow channel having a second end portion constructed for fluid connection to a processing system;
    a container constructed to retain a liquid therein;
    a second flow channel having a first end portion fluidly connected to said container, said second flow channel having a second end portion in fluid communication with said additive reservoir;
    a filter constructed to sterilize a liquid contained in said container, said filter disposed between said additive reservoir and said container; and
    a first valve constructed to control flow through said second flow channel.

2. An apparatus in accordance with claim 1, wherein said apparatus further comprises a second valve constructed to control flow through said first flow channel.

3. An apparatus in accordance with claim 1, wherein said apparatus further comprises an indicia constructed to measure a volume of liquid in said additive reservoir.

4. An apparatus in accordance with claim 3, wherein said indicia is disposed on said additive reservoir.

5. An apparatus in accordance with claim 3, wherein said indicia comprises a movable calibration scale.

6. A method for adding a sterile liquid to a processing system, said method comprising the steps of:
    providing an apparatus for adding a quantity of a liquid to a processing system, said apparatus comprising:
        an additive reservoir constructed to retain a liquid therein;
        a vent having a gas filter constructed to sterilize a gas flowing through said vent, said vent disposed in fluid communication with said additive reservoir;
        a first flow channel having a first end portion fluidly connected to said additive reservoir, said first flow channel having a second end portion constructed for fluid connection to a processing system;
        a container constructed to retain a liquid therein;
        a second flow channel having a first end portion fluidly connected to said container, said second flow channel having a second end portion in fluid communication said additive reservoir;
        a filter constructed to sterilize a liquid contained in said container, said filter disposed between said additive reservoir and said container; and
        a first valve constructed to control flow through said second flow channel;
    connecting said second end portion of said first flow channel to a processing system to which a liquid is to be added;

opening said first valve and flowing a liquid from said container, through said filter, and into said additive reservoir;

directing a selected quantity of said liquid from said additive reservoir into said system.

7. A method in accordance with claim 6, wherein said apparatus further comprises a second valve constructed to control flow through said first flow channel, said second valve being open during said step of directing a selected quantity of said liquid from said additive reservoir into said system, said method further including the steps of:

closing said second valve prior to opening said first valve and flowing a liquid from said container, through said filter, and into said additive reservoir; and closing said first valve prior to directing a measured quantity of said liquid from said additive reservoir into said system.

8. A system for aseptically processing a liquid composition, said system comprising:

a liquid processing system;

an additive reservoir constructed to retain a liquid therein;

a vent having a gas filter constructed to sterilize a gas flowing through said vent, said vent disposed in fluid communication with said additive reservoir;

a first flow channel having a first end portion fluidly connected to said additive reservoir, said first flow channel having a second end portion fluidly connected to said processing system;

a container constructed to retain a liquid therein;

a second flow channel having a first end portion fluidly connected to said container, said second flow channel having a second end portion in fluid communication with said additive reservoir;

a filter constructed to sterilize a liquid contained in said container, said filter disposed between said additive reservoir and said container; and a first valve constructed to control flow through said second flow channel.

* * * * *